United States Patent [19]

Lööf et al.

[11] Patent Number: 5,098,293
[45] Date of Patent: Mar. 24, 1992

[54] DEVICE FOR IMPLANT WORK

[75] Inventors: Lennart Lööf, Göteborg, Sweden; Pierre-Luc Maillefer, Ballaigues, Switzerland

[73] Assignee: Nobelpharma AB, Gothenburg, Sweden

[21] Appl. No.: 689,477

[22] Filed: Apr. 23, 1991

[30] Foreign Application Priority Data

Apr. 24, 1990 [SE] Sweden .................... 9001472

[51] Int. Cl.⁵ .............................. A61C 3/02
[52] U.S. Cl. ...................... 433/165; 408/226
[58] Field of Search .......... 433/165, 166, 225; 408/226

[56] References Cited

U.S. PATENT DOCUMENTS

| | | | |
|---|---|---|---|
| 1,471,702 | 10/1923 | Mulac | 408/226 |
| 3,576,076 | 4/1971 | Weissman | 433/165 |
| 4,255,145 | 3/1981 | Weissman | 433/165 |

Primary Examiner—John J. Wilson
Attorney, Agent, or Firm—Pollock, Vande Sande & Priddy

[57] ABSTRACT

In connection with implant work on the dentine, a machining instrument is used which is provided with an attachment part for attachment to a rotary unit or for attachment to extension unit, which in turn can be applied to the rotary unit. The extension unit has a thickened central section which is provided with a recess or opening in which an inclined surface is arranged. In the applied position of a machining instrument, one surface of its attachment part is set against the inclined surface of the extension unit. The extension unit and the machining instrument are rotationally-fixed with respect to each other. Moreover, a locking effect is achieved between the extension unit and the machining instrument as a result of a secure wedging effect obtained by means of the inclined surface.

12 Claims, 2 Drawing Sheets

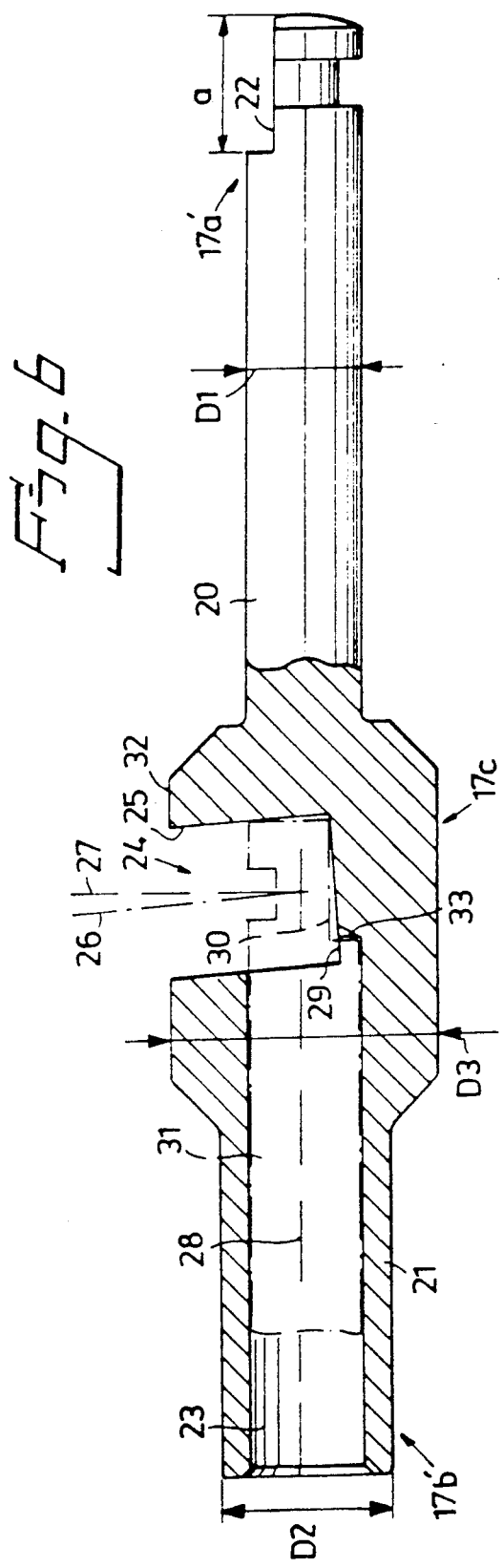
Fig. 6
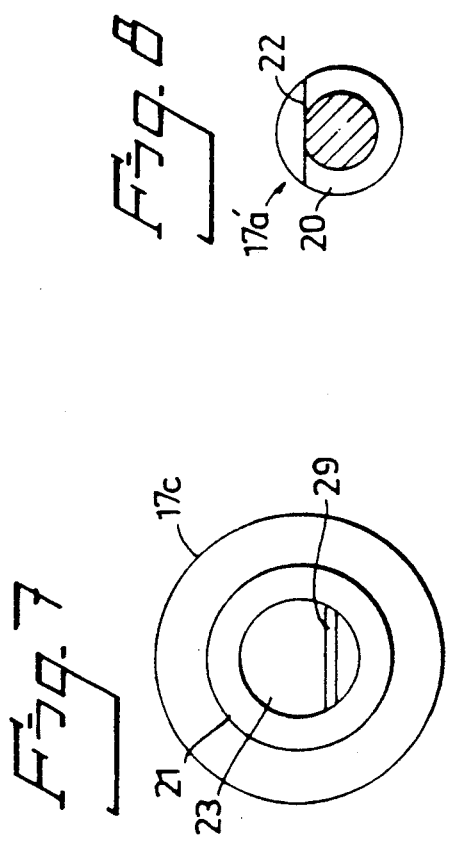
Fig. 8
Fig. 7

DEVICE FOR IMPLANT WORK

TECHNICAL FIELD

The present invention relates to a device for reducing the number of different lengths needed in machining instruments, in the form of drills, grinding instruments, etc. and the like, in connection with implant work on the jaw/dentine or other part of the body. Each machining instrument is designed with a part for attachment to a rotary unit (tool), by means of which each machining instrument can be rotated.

BACKGROUND OF THE INVENTION

Due of the differences in the drilling (machining) depth and variable accessibility in implant work, there is a requirement for equipment permitting considerable variation in the lengths of the machining instruments/drills. Sets comprising a large number of machining instruments/drills have therefore been made available hitherto, from which sets instruments/drills of a suitable length have been chosen as the work progresses. A large number of machining instruments complicates the work and is moreover expensive to provide.

The present invention makes use of the knowledge that one or more extension units between the rotary unit and each machining instrument can reduce the number of lengths needed in the machining instruments.

SUMMARY OF THE INVENTION

The present invention provides an extension unit for the machining instruments which itself is available in several lengths, if so desired. The extension unit should be easy to arrange in the rotary unit and be adapted to receive and bear, at least in a rotationally fixed manner, machining instruments of different types and lengths. The functioning should be simple and straightforward from the handling point of view, so that a reliable anchoring of the extension unit in the rotary unit and of each machining instrument in the extension unit can be achieved at all times. The extension unit must have a smooth structure which does not have an adverse effect on the work being carried out. In addition, its manufacture should be technically simple and economically attractive.

The present invention proposes a device which meets the requirements mentioned above. The device comprises an extension unit which, at its first end, is designed with, or is connected to, an attachment part which corresponds to the attachment part on each machining instrument and through which the extension unit can be connected to rotated by the rotary unit. The extension unit is moreover designed with a bearing recess extending from its other end for each machining instrument the machining instrument can be inserted into the bearing recess through its attachment part to provide a rotationally fixed cooperation between the attachment part and the extension part through a surface on the attachment part and an actuation surface in the extension unit. The extension unit is preferably designed with a central section situated between the first and second ends, through which section the longitudinal insertion position of each machining instrument in the extension unit can be indicated, and each machining instrument applied in the unit can be acted upon in conjunction with its separation from the extension unit.

In one embodiment, the actuation surface also forms a secure wedging surface, by means of which each machining instrument can be locked in the direction of its longitudinal displacement. As seen in the longitudinal and transverse directions of the extension unit, the actuation surface is preferably designed straight. It can cooperate with a similarly straight and corresponding opposite surface on the attachment part of each machining instrument. Moreover, the actuation surface is inclined in the insertion direction and widens towards the other end of the extension unit at a small angle which can be chosen from within the range of 2°-6°. The angle is preferably about 4°. The corresponding opposite surface on the attachment part of each machining instrument extends substantially parallel to the longitudinal axis of the machining instrument. By using this section, which is preferably thickened in relation to the other parts of the extension unit, an opening can be arranged in connection with the combined rotational actuation and secure wedging surface. The opening allows for visual indication of the insertion position of each machining instrument in the extension unit. The opening also provides for a simple separation possibility for an applied machining instrument. The opening also means that the actuation surface can be given a position which is advantageous from the production point of view. The opening is preferably made by means of an inclined segment-shaped cutting being milled in the central section. The bearing recess is preferably arranged centrally in the extension unit, along whose longitudinal axis the recess extends towards the opening. By means of the inclination of the recess/opening, the inclined surface widening towards the other end of the extension unit can be obtained.

The extension unit is preferably made with two cylindrical parts which project from each side of the central section. The cylindrical part supporting the attachment part of the extension unit is designed with a first, preferably smallest diameter. The part supporting the bearing recess is designed with a diameter which exceeds the first diameter. The section has a diameter or a peripheral dimension which exceeds the second diameter.

The present invention design affords a smooth, easy-to-handle and reliably functioning extension unit which substantially reduces the number of machining instruments in the sets used. The reduction in machining instruments and the economical production of the extension unit as such affords significant economical advantages in medical care. Handling is extremely simple since the extension unit is applied in the rotary unit in the same way as each machining instrument. Each machining instrument can be inserted easily into the extension unit and can be securely arranged in the extension unit by means of the applied secure wedging principle. The separation of each machining instrument from each extension unit can be carried out easily, for example by applying a finger, tool, and the like through the opening for effecting the separation. The use of the inclined surface can result in the machining instrument becoming slightly out-of-line about its axis of rotation. However, this has no importance, since the work in question involves rotating at a low speed, for example about 2000 rpm. The extension unit can be produced from a single piece which has a thicker central section and two substantially cylindrical parts, of which the one is made with attachment members and other with a bearing recess. The central section is provided with an inclined and advantageously sector-shaped opening giving onto one side of the unit.

BRIEF DESCRIPTION OF THE DRAWINGS

FIG. 6 shows in a longitudinal section a detailed design of the extension unit according to the present invention.

FIG. 7 shows a first end view of the unit according to FIG. 6, and

FIG. 8 shows a second end view of the unit according to FIG. 6.

DETAILED DESCRIPTION OF THE PREFERRED EMBODIMENTS

Figure 1:
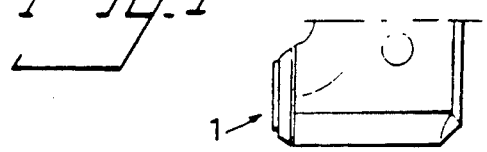
FIG. 1 shows a basic diagram of parts of a known rotary unit.

FIG. 1 shows the head of a rotary unit 1 which is known and which is designed to support different types of machining tools/drills 2-12 according to FIGS. 2-5. Each machining instrument of 2-12 comprises an attachment part 2a which is designed with a rear flange 13 and a depression (groove) 14 arranged behind the latter. Each machining instrument comprises a head 15 with an associated part 16 effecting the machining. Since the machining instruments themselves, like the rotary unit, are already well known, they will not be described in detail here. Each machining instrument can be applied in an extension unit 17. The basic design of the extension unit is the same in FIGS. 2-5, for which reason only the extension unit in FIG. 2 will be described in detail. The extension unit 17 is designed with an attachment part 17a which in principle corresponds to the design of the attachment part 2a in each machining instrument. In this way the attachment part can be applied in the rotation unit 1 in a manner corresponding to each machining instrument. The rear flange on the attachment part of the extension unit has been given the reference 18 and the following groove reference 19. The extension unit supports the machining instrument 2' at its end 17b in accordance with what is stated below.

Figure 2:
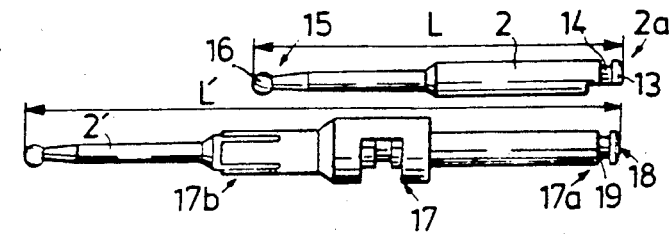
FIG. 2 shows, from the side, a first type a machining instrument, with one machining instrument shown separate and one machining instrument shown applied to an extension unit.

FIG. 2 shows that it is possible to obtain different (two) drill lengths L and L' by means of a machining instrument 2 and an extension unit 17. In the first-mentioned case, the machining instrument is applied directly in the rotary unit 1 and in the second case the machining instrument is applied in the extension unit which in turn is applied or has been applied in the rotary unit 1.

Figure 3:
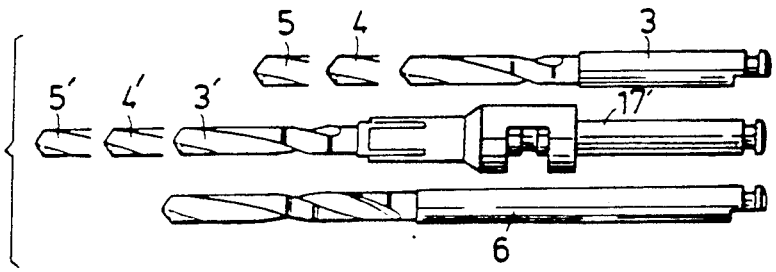
FIG. 3 shows a second type of machining instrument, in which the machining instruments themselves are available in a number of lengths (for example 4) and each machining instrument can in turn be applied to an extension unit.

FIG. 3 shows that it is possible to obtain seven different machining instrument lengths by means of four machining instruments 3, 4, 5 and 6 and one extension unit 17'.

Figure 4:
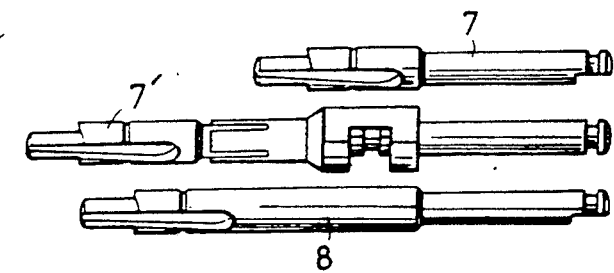
FIG. 4 shows a third type of machining instrument which is shown separate and also applied to an extension unit.

FIG. 4 shows that it is possible to obtain three different machining instrument lengths by means of two machining instruments 7, 8 and one extension unit.

Figure 5:
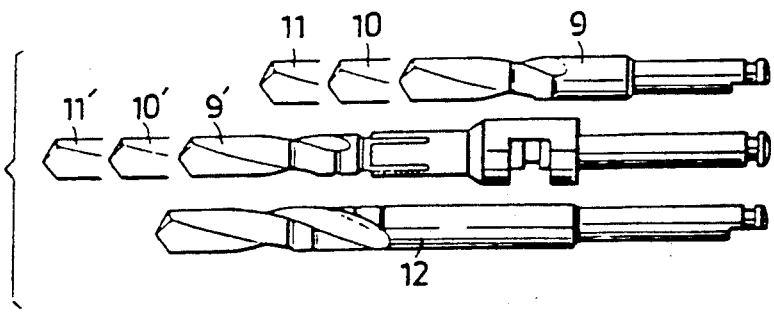
FIG. 5 shows a fourth type of machining instrument.

FIG. 5 shows a case corresponding to the case according to FIG. 3. FIGS. 2-5 also show different types of machining instruments.

According to FIG. 6, the extension unit is made up of a first cylindrical part 20 with a diameter D1, a second cylindrical part 21 with a second diameter D2 and a central section 17c arranged between the parts 20 and 21. As emerges from FIGS. 6 and 8, a segment-shaped part is removed from the cylindrical section 20. The length of the removed part is indicated by a. By means of the segment-shaped recess, a surface 22 is formed which is straight in the longitudinal and transverse directions of the extension unit. A bearing recess 23 extends centrally and in the longitudinal direction of the extension unit. The section 17c is provided with an opening 24 which has been produced by means of an inclined recess/cutting, whose wall is indicated by 25. The recess is inclined so that its axis 26 slopes in relation to the perpendicular 27 of the longitudinal axis 28 of the extension unit. The bottom surface 29 of the hole thus slopes in relation to the longitudinal axis 28. The bottom surface 29 is preferably straight in the longitudinal and transverse directions of the extension unit and in addition slopes in the longitudinal section shown in FIG. 6 in relation to the longitudinal axis 28. The surface widens towards the second end 17b'. The degree of sloping can be within the range of 2°-6°, and in the case shown it is chosen to be about 4°. The said central section 17c is preferably thicker than the parts 20 and 21. In a preferred embodiment, the diameter D1 is smaller than the diameter D2, which in turn is smaller than the diameter D3 (in the circular central section 17c) or peripheral dimension (in the non-circular central section) of the central section 17c.

A surface 30 on an attachment part 31 on a machining instrument applied in the extension unit can be set against the inclined or sloping surface 29. The surface 30 has a design substantially to the surface 22 on the extension unit. The surface 30 is thus straight in the longitudinal and transverse directions of the machining instrument and is substantially parallel to the longitudinal axis 28 in the longitudinal section shown in FIG. 6. The straight surfaces 29 and 30 therefore form a rotationally fixed contact between the extension unit and the machining instrument applied in the latter. As a result of the inclination or slope of the surface 29, a locking effect is also achieved in the longitudinal direction of the machining instrument, which coincides with the longitudinal axis 28. The machining instrument can be pressed into its position shown in FIG. 6 by taking hold of the head of the machining instrument, see 15 in FIG. 2 and moving the machining instrument into the recess 23 via its attachment part 31. The opening affords a visual indication of the longitudinal displacement position of the machining instrument in relation to the extension unit. The opening-recess 24 can also serve as a separation access point upon separation of the machining instrument from the extension unit. The cutting or recess 24 is designed in such a way that it extends from the outside (outer surface) 32 of the section 17c down under the center axis 28. The recess 23 contacts the recess 24 at their inner parts. A segment-shaped, radially extending surface 33 is arranged at the transition.

The extension unit is about 30 mm long and the recess 24 has a length of about 3 mm. The approximate values for the diameters D1-D3 are 2.35, 3.5 and 5.5 respectively. The recess 23 is designed in such a way that it provides good guiding for each machining instrument.

The invention is not limited to the embodiment shown above by way of example, but can be subjected to modifications within the scope of the following patent claims and the inventive concept.

We claim:

1. An apparatus for reducing the number of different lengths required in machining instruments used in connection with implant work the machining instrument including an attachment part for attachment to a rotary unit for rotation of the machining instrument, said apparatus comprising:

an extension unit including a first end, a second end and a central section extending therebetween, an attachment element of said extension unit provided at said first end and corresponding to said attachment part of the machining instrument, said attachment element allowing for mounting of said extension unit onto said rotating unit;

a bearing recess extending from said second end of said extension unit for receiving the attachment part of the machining instrument therein;

means provided in said central section of said extension unit for indicating longitudinal insertion position of said attachment part of the machining instrument inside said extension unit and for access to the inserted machining instrument for effecting separation of the machining instrument from said extension unit.

an actuation surface provided in said bearing recess of said extension unit, said actuation surface being substantially straight in the longitudinal and transverse direction of said extension unit and a substantially straight corresponding opposite surface on the attachment part of the machining instrument, said actuation surface being inclined along the longitudinal axis of said extension unit, said corresponding opposite surface being substantially parallel with the longitudinal axis of the extension unit, wherein an angle of inclination is so selected that a wedging action occurs between said actuation and opposite surface upon insertion of said attachment part into said recess of said extension unit to thereby fixedly connect said machining instrument within said extension unit.

2. An apparatus according to claim 1 wherein said angle of inclination is selected from the range of about 2° to about 6°.

3. An apparatus according to claim 2 wherein said means in said central section includes an opening extending therethrough in a direction transverse to the longitudinal axis of said extension unit and wherein said actuation surface is situated at the location of said opening.

4. An apparatus according to claim 3 wherein said opening in said central section is formed by a segment-shaped recess which is inclined towards the longitudinal axis of the extension unit in relation to the perpendicular.

5. An apparatus according to claim 4 wherein said segment-shaped recess slopes about 2° to about 6°, with respect to the perpendicular, as seen in a longitudinal section through said extension unit.

6. An apparatus according to claim 3 wherein the bearing recess extends centrally through a portion of said extension unit in the longitudinal direction thereof and an inner end thereof merges into said opening.

7. An apparatus according to claim 3 wherein said inclined actuation surface merges into a radially extending segment-shaped surface at the bottom part of the segment-shaped opening.

8. An apparatus according to claim 1 wherein said angle of inclination is about 4°.

9. An apparatus according to claim 1 wherein said attachment part and said attachment element each comprises a flange situated at the first end of said extension unit and the machining instrument respectively, a depression arranged behind the flange, and a segment-shaped part removed therefrom in order to provide a surface which is straight in the longitudinal and transverse directions.

10. An apparatus according to claim 1 wherein said extension unit, at the first end, is substantially cylindrical and has a first diameter, at the second end is also substantially cylindrical and has a second diameter which exceeds the first diameter and wherein said central section has a third diameter which largely exceeds the second diameter.

11. An apparatus for reducing the number of different lengths required in machining instruments used in connection with implant work each machining instrument including an attachment part for attachment to a rotary unit for rotation of the instrument, said apparatus comprising:

an extension unit including a first end, and a second end and a central section extending therebetween, an attachment element provided at said first end of said extension unit and corresponding to said attachment part of the machining instrument, said attachment element allowing for mounting of said extension unit onto the rotary unit;

a bearing recess extending from said second end of said extension unit for receiving the attachment part of the machining instrument therein;

means provided in said central section of said extension unit for indicating longitudinal insertion position of the attachment part inside said extension unit and for access to the inserted machining instrument for effecting separation of the machining instrument from said extension unit.

an actuation surface provided on said extension unit, said actuation surface being substantially straight in the longitudinal and transverse direction of said extension unit and a substantially straight corresponding opposite surface on the attachment part of the machining instrument, said actuation surface being inclined along the longitudinal axis of said extension unit at an angle of about 2° to about 6° towards said second end of said extension unit, said corresponding opposite surface being substantially parallel with respect to the longitudinal axis of said extension unit, wherein upon insertion of said attachment part of said instrument into said recess of said extension unit said machining instrument is locked within said extension unit.

12. An apparatus according to claim 11 wherein said opening in said central section is formed by a segment-shaped recess which is inclined towards the longitudinal axis of the extension unit in relation to the perpendicular.

* * * * *